United States Patent [19]

Cassinelli et al.

[11] 4,309,503
[45] Jan. 5, 1982

[54] PREPARATION OF 11-DEOXY ANTHRACYCLINE ANTIBIOTICS

[75] Inventors: Giuseppe Cassinelli, Pavia; Arpad Grein, Milan; Sergio Merli, Milan; Giovanni Rivola, Milan, all of Italy

[73] Assignee: Farmitalia Carlo Erba S.p.A., Milan, Italy

[21] Appl. No.: 82,294

[22] Filed: Oct. 5, 1979

Related U.S. Application Data

[62] Division of Ser. No. 9,650, Feb. 5, 1979, Pat. No. 4,247,545.

[30] Foreign Application Priority Data

Feb. 17, 1978 [GB] United Kingdom ............... 5246/78

[51] Int. Cl.³ .............................................. C12P 19/56
[52] U.S. Cl. .................................... 435/78; 435/172; 435/253; 536/17 A; 424/181
[58] Field of Search ......................... 435/78, 172, 253

[56] References Cited

U.S. PATENT DOCUMENTS 3,686,163  8/1972  Arcamone et al. ............... 435/78
3,993,544  11/1976  Demain et al. .................. 435/172

OTHER PUBLICATIONS

Lamanna et al., Basic Bacteriology, Its Biological and Chemical Background, The Williams & Williams Co., pp. 723–727 (1965).

Metzler, Biochemistry, The Chemical Reactions of Living Cells, Academic Press pp. 945 & 946 (1977).

*Primary Examiner*—Alvin E. Tanenholtz
*Attorney, Agent, or Firm*—Hubbell, Cohen, Stiefel & Gross

[57]  ABSTRACT

Anthracycling antibiotics of the formula:

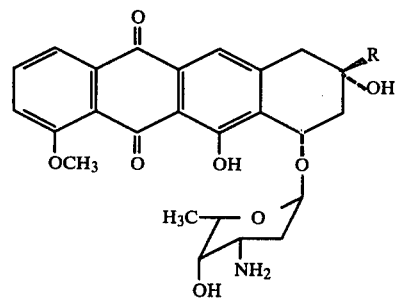

wherein R is —CO—CH$_2$OH, —CHOH—CH$_3$, —CO—CH$_3$ or —CH$_2$—CH$_3$ having antitumor and antibacterial activity are prepared by culturing a new mutant strain of microorganism designated as *Macromonospora peucetica* sp. *nova* and which has been deposited with the American Type Culture Collection under numbr No. 31366 ATCC.

6 Claims, No Drawings

PREPARATION OF 11-DEOXY ANTHRACYCLINE ANTIBIOTICS

This is a division of application Ser. No. 9,650, filed Feb. 5, 1979, now U.S. Pat. No. 4,247,545.

BACKGROUND OF THE INVENTION

1. Field of the Invention

The present invention relates to anthracycline antibiotics which are 11-deoxy analogues of the known anthracycline antibiotics daunomycin and adriamycin*, their aglycones, methods of preparing same, the use thereof, a new strain of microorganism used to make said antibiotics and a method of making the new strain of microorganism.

*Daunomycin and adriamycin are also known respectively as daunorubicin and doxorubicin.

2. The Prior Art

Daunomycin and adriamycin are known antitumor antibiotics of the anthracycline series. Their aglycones are, of course, also known.

The microorganism, Streptomyces peucetius var. cacsins, is also known; see, Arcamone et al., Biotechnol. Biogen., 1969, X1, 1101–1110.

SUMMARY OF THE INVENTION

The invention provides, in one aspect thereof, a new class of anthracycline antibiotics, hereinafter designated as glycosides A, B, C and D, which are 11-deoxy derivatives of daunomycin and adriamycin, as well as their respective aglycones. The new 11-deoxy derivatives have the following formula:

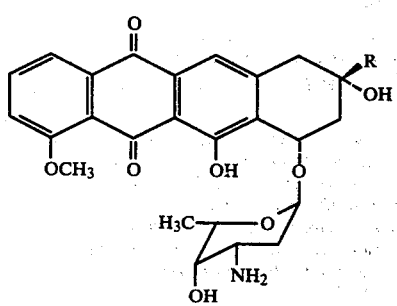

I-IV wherein R is —COCH$_2$OH(I), —CHOH—CH$_3$(II), —CO—CH$_3$(III) or —CH$_2$—CH$_3$(IV).

Glycoside A has the formula (I) and is 11-deoxy-adriamycin;

Glycoside B has the formula (II) and is 11-deoxy-13-dihydrodaunomycin;

Glycoside C has the formula (III) and is 11-deoxy-daunomycin; and

Glycoside D has the formula (IV) and is 11-deoxy-13-deoxo-daunomycin.

The respective aglycones which are obtained from the glycosides by aqueous acid hydrolysis to remove the sugar moiety, i.e., daunosamine have the formula:

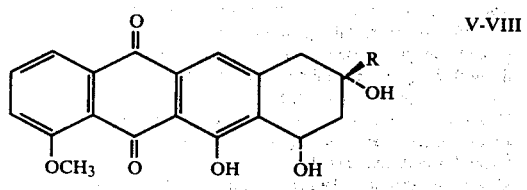

V-VIII wherein R is —COCH$_2$OH(V), —CHOH—CH$_3$(VI), —CO—CH$_3$(VII) or —CH$_2$—CH$_3$(VIII).

The aglycone of glycoside A has the formula (V) and is 11-deoxy-adriamycinone;

The aglycone of glycoside B has the formula (VI) and is 11-deoxy-13-dihydro-daunomycinone;

The aglycone of glycoside C has the formula (VII) and is 11-deoxy-daunomycinone; and The aglycone of glycoside D has the formula (VIII) and is 11-deoxy-13-deoxo-daunomycinone.

In another aspect, the invention provides methods of preparing the glycosides A, B, C and D which method comprises culturing a new mutant strain of the microorganism Streptomyces peucetius var. caesius which produces the glycosides A, B, C and D, and recovering same from the culture medium.

In yet another aspect, the invention provides a method for producing the new mutant strain of said microorganism which comprises subjecting same to a mutagenic treatment with N-methyl-N'-nitro-N-nitrosoguanidine.

In still another aspect, the invention provides said new mutant strain of the microorganism which has been designated number B211 F.I.* of the Farmitalia Collection of Microorganisms. This new mutant strain has been demonstrated to be a new species of the genus Micromonospora. It has also been designated as Micromonospora peucetica sp. nova.

Samples of the new strain have been deposited with the American Type Culture Collection Under No. 31366 ATCC; with the Deutsche Sammlung Mikroorganismen under No. 1190 DSM; and with the Japanese Fermentation Research Institute under No. 4363 FRI.

In still another aspect, the invention provides pharmaceutical compositions comprising said glycosides A, B C or D in combination with an inert carrier therefor.

Finally, the invention provides methods of treating certain mammalian tumors (L 1210 and P 388 leukemia) and bacterial infections using the new glycosides.

By way of summary then, the present invention includes the new anthracycline glycoside antibiotics designated A, B, C and D, both in dilute form as crude concentrates and in pure crystalline form, and the corresponding aglycones. The invention also includes processes for the production of these compounds by fermentation of a mutant strain of Streptomyces peucetius var. caesius, and their recovery, concentration, purification and salt preparation.

The new anthracycline glycosides display antitumor and antibacterial activity. More particularly, glycosides A and C are useful as antitumor agents in experimental animals.

The new microorganism used in the invention is obtained by a mutagenic treatment with N-methyl-N'-nitro-N-nitrosoguanidine of Streptomyces peucetius var. caesius. As in the case of many antibiotic-producing cultures, fermentation of strain B211 F.I. results in the production of a mixture or a complex of components. Four bioactive anthracycline components the glycosides A, B, C and D, have been separated from that complex.

The present anthracycline glycosides all contain daunosamine (3-amino-2,3,6-trideoxy-L-lyxo-hexose), which is the amino sugar component of daunomycin and adriamycin (F. Arcamone, G. Cassinelli, P. Orezzi, G. Franceschi and R. Mondelli, J. Am. Chem. Soc., 86, 5335, 1964 and U.S. Pat. No. 3,590,028). The structures of the new glycosides were determined by analysis of their infrared, ultraviolet, visible, mass and magnetic resonance spectra and are all in agreement with the chemical and physical data provided hereinbelow.

The new anthracycline glycoside complex and its individual components form salts with both acids and bases, and pharmaceutically acceptable salts of the complex and its components are also included within the scope of the invention. Examples of such pharmaceutically acceptable salts include salts with acids such as hydrochloric, sulphuric, nitric, and phosphoric, and with metallic cations, for example, alkali metal or alkaline earth metal cations such as sodium, potassium, calcium and magnesium, and also with other cations such as trivalent iron cations.

DETAILED DESCRIPTION OF THE INVENTION

The Microorganism

Microscopic properties of strain B 211 F.I.

The spores of B 211 F.I. are of the following size: 0.9–1.1×1.1–1.6μ. They are borne singly or very frequently in pairs, and only rarely as clusters, terminally on short sporophors arising monopodially as branches on long, randomly produced hyphae, 0.5–0.9μ in thickness. Rarely are sessile spores observed. No polymorphic forms are produced and aerial mycelium is absent.

Macroscopic properties of strain B 211 F.I.

The cultural characteristics of strain B 211 F.I. are given below in Table 1. Growth of the microorganism is generally good on organic media, not quite as good on synthetic media; on the former, it is generally raised and ridged, rather moist but non-slimy in appearance.

The sporulation layer turns the orange-terra cotta colore vegetative mycelium brown to almost black upon ageing. No soluble pigment is generally produced. No growth is observed at temperatures above 40° C. The physiological and biochemical properties of strain B 211 F.I. are given below in Table 2.

Identification and classification of strain B 211 F.I.

The strain B 211 F.I. is clearly referrable to the genus Micromonospora RSKOV (RSKOV, J. "Investigations into the Morphology of the Ray Fungi", Levin and Maunksgaard, Copenhagen, 1923, page 171) of the order Actinomycetales, on the basis of its morphological and cultural characteristics. However, careful comparative examination of the characteristic described and reported by WAKSMAN, S. A. ("The Actinomycetes" Vol. 2–1961, Williams and Wilkins Co. Baltimore and "The Actinomycetes; A Summary of Current Knowledge", 1967, Ronald Press Co.), LEUDEMANN and BRODSKY (1963) and LUEDEMANN, G. ("Micromonospora Taxonomy" Advances in Applied Microbiology, 1970, 11, 101–133) for known species belonging to this genus, with those shown by strain B 211 F.I. did not enable us to identify the present strain with any of the named species listed for the above-mentioned genus. Because of its peculiar carbohydrate utilization pattern, and because it produces new anthracyclines, it may be concluded that strain B 211 F.I. differs from all previously described species of this genus, and is a new species. This new species has been given the binomial designation of *Micromonospora peucetica* sp. nova.

TABLE 1

Cultural characteristics of Strain B 211 F.I. on various media according to Waksman, 1961, supra, where not specified otherwise.

| Medium | Response |
| --- | --- |
| Bennett's agar | Growth good, raised and ridged, color orange to terra cotta or coral red, turning to black on ageing. |
| Emerson's agar | Growth fair, raised and ridged. Colorless to light terra cotta throughout turning brown on ageing. |
| Glucose-asparagine agar | Growth good, flat, color light terra cotta throughout. |
| 1% NZ-amine type A, 1% glycose + agar (LUEDEMANN G.M. et. al. Antimicrobial Agents, 1963, pp. 116-124) | Growth good, raised and ridged. Color from orange terra cotta to bright red, turning brown to black on ageing. |
| Glucose-yeast extract agar | Growth poor, raised and ridged. Color light terra cotta throughout. |
| Starch-casein agar | Growth good, flat. Color terra cotta throughout. |
| Gelatin agar | Growth poor, raised and ridged. Color terra cotta to bright red. |
| Tyrosine agar (GORDON, R.D. and SMITH, M.L., J. Bacteriol., 69, 1955, pp. 147-150) | Growth good, raised and ridged. Bright terra cotta color at first, deep reddish turning copper brown to almost black, on ageing. A deep brown soluble pigment is produced. |
| Yeast extract-L-tyrosine agar | Growth fair flat. Color brown, a deep reddish to coffee brown soluble pigment is produced. |
| Pepton-iron agar (TRESNER, H.D. and DANGA, F., J. Bacteriol. 76, 1958, pp. 239-244) | Growth good, raised and ridged. Color light terra cotta throughout. |
| Potato-glucose agar | Growth moderate, raised and ridged. Color from terra cotta to brown turning almost black on ageing. |
| Czapeck's agar | Growth poor, flat. Color light terra cotta turning black on ageing. |
| Glycerol-glycine agar | Growth moderate, flat. At first colorless, turning olive green to deep green on ageing. |
| Inorganic-salts-starch agar (PRIDHAM, T.C. et al, Antibiotics Annual 1956/1957, pp. 947-953) | Growth fair, flat. Color from rose to terra cotta turning orange brown on ageing. |
| Glycerol-asparagine agar | Growth poor, flat. Color light terra cotta turning almost black on ageing. |
| SA agar (see for composition maintenance medium in Example 1) | Growth good, raised and ridged. Color at first creamy to honey-like turning later terra cotta and becoming slightly brownish on ageing. Sometimes a yellow soluble |

TABLE 1-continued

Cultural characteristics of Strain B 211 F.I. on various media according to Waksman, 1961, supra, where not specified otherwise.

| Medium | Response |
|---|---|
| | pigment turning slightly brown on ageing is observed. |

TABLE 2

Physiological and biochemical properties of Strain B 211 F.I.*

| Utilization of: | | |
|---|---|---|
| | glucose | + |
| | sucrose | + |
| | D-xylose | + |
| | M-mannitol | + |
| | M-inositol | + |
| | L-arabinose | + |
| | D-fructose | + |
| | Adonitol | + |
| | lactose | + |
| | d (+) mannose | + |
| | maltose | + |
| | raffinose | + |
| | L-rhamnose | + |
| | alpha-alpha-trehalose | + |
| | esculin | + |
| | glycerol | + |
| | Na—citrate | + |
| | NH$_4$—succinate | + |
| | Na—acetate | + |
| | NH$_4$—tartrate | + |
| | glycogen | + |
| | paraffin | − |
| Negative control | | − |
| Liquefaction of gelatin | | + |
| Tyrosine decomposition | | + |
| Malanin formation | | + |
| Hydrolysis of starch | | + |
| H$_2$S formation | | − |
| Nitrate reduction | | + |
| Milk (pepton- and coag.) | | |
| Antibiotics produced: new anthracyclines | | |

+ = positive reaction
− = negative reaction
*The medium for the carbohydrate utilization test is as described by R. D. Gordon and M. L. Smith, supra.
*The media used for the other physiological reactions are those reported by S. A. Waksman, 1961, supra.

FERMENTATION PROCESS

The production of the new glycosides is carried out by conventional, well known methods, and comprises culturing the microorganism in a previously sterilized liquid culture medium under aerobic conditions at a temperature of from 25° C. to 37° C. (preferably at 28° C.) for from 5 to 30 days (preferably 15 days) and at a pH which initially is from 6.5 to 7.0 and which, at the end of the fermentation period is from 6.5 to 8.0.

The culture medium consists of a carbon and a nitrogen source as well as mineral salts. The carbon source may, for example, be starch, dextrin, glucose, glycerin, mannite, maltose, corn steep liquor, distillers solubles, soybean oil or soybean meal. The nitrogen source, besides those of the above-mentioned complex substances which contain nitrogen, may be for example, dry yeast, meat pepton or casein. Good results are even obtained by using ammonium salts such as ammonium nitrate, ammonium sulphates and diammonium phosphates. The mineral salts vary according to the medium employed. In a medium containing complex substances such as various meals and fermentation residues, the addition of the calcium carbonate and sodium or potassium phosphates has proved useful. In media containing glucose, or ammonium salts, much higher levels of mineral salts such as potassium, sodium or calcium salts, and additions of trace elements such as iron, zinc, copper, magnesium and manganese are necessary. The fermentation may be carried out in Erlenmeyer flasks or in laboratory or industrial fermenters of various capacities.

ANALYTICAL METHODS

Samples of the fermentation broth and crude preparations are subjected to paper chromatography using Whatman No. 1 paper, buffered with M/15 phosphate buffer at pH 5.4, employing as the eluant a mixture of n-propanol:ethyl acetate:water (7:1:2). The paper strips are bioautographed against Bacillus subtilis, and four antibiotic components were found to occur. These are designated glycoside A (Rf 0.30), B (Rf 0.50), C Rf 0.55) and D (Rf 0.65).

Crude preparations are subjected to thin layer chromatography (TLC) using pre-coated TLC plates of silica gel 60-F-254 (Merck) and as the eluant, a mixture of chloroform:methanol:acetic acid:water (80:20:14:6). Four yellow compounds occur, and they correspond to glycoside A (Rf 0.50), B (Rf 0.55), C (Rf 0.65) and D (Rf 0.70) respectively.

A quantitative estimation of the total yellow constituents present in the fermentation broth can be made by the following method. To a sample of broth, adjusted to pH 8.6, two volumes of chloroform:methanol (9:1) are added. The resulting mixture is sonicated for 1 minute at room temperature. On a sample of the organic phase, diluted with acidic methanol, the total content of the yellow anthracyclines and of their aglycones can be spectrophotometrically determined at 418 nm. On a sample of the organic phase, concentrated under reduced pressure, quantitative determination of the single glycosides can be obtained by preparative TLC using the above reported system. The different yellow zones are scraped off and eluted with methanol. Each constituent is sectrophotometrically determined at 418 nm. Glycoside A is usually the major constituent in the fermentation broths.

ISOLATION PROCEDURE

After the fermentation, the active compounds are contained in the mycelia and in the fermentation liquor. The anthracycline antibiotic complex can be extracted at pH 8.5–9.0 in the form of the free bases from the culture broth "in toto" with a water immiscible organic solvent such as butanol, methyl isobutyl ketone, chloroform, methylene dichloride or ethyl acetate. Preferably, the mycelia and the fermentation liquor are separated by filtration at pH 4 with the aid of diatomaceous earth, and then extracted separately.

The filtration cake is extracted with a mixture of a water-soluble solvent, such as acetone, methanol or other lower alcohol, and an 0.1 N aqueous solution of an inorganic or organic acid, such as hydrochloric acid, sulphuric acid or acetic acid. Generally, a mixture of acetone: 0.1 N hydrochloric acid in a ratio 4:1 by volume is employed. The mycelia extracts are collected, adjusted to pH 4, and then concentrated under reduced pressure. The aqueous concentrate is combined with the filtered broth, adjusted to pH 8.5–9.0, then extracted with a water immiscible organic solvent, preferably chloroform or n-butanol. The extracts are concentrated under reduced pressure and the anthracycline complex is precipitated by addition of five volumes of n-hexane. The constituents of the crude complex are then fractionated and purified by column chromatography.

acetate they form red solutions. All these properties and the absorption spectra in the ultraviolet and visible regions, indicate that these new compounds are anthracycline antibiotics. The chemical and physical properties of glycosides A, B, C and D, isolated as the hydrochlorides are given in Table 3.

TABLE 3

| | Chemical and physical properties of Glycosides, A, B, C and D | | | |
|---|---|---|---|---|
| PROPERTY | GLYCOSIDE A. HCl | GLYCOSIDE B. HCl | GLYCOSIDE C. HCl | GLYCOSIDE D. HCl |
| Melting Point | 171°–173° (dec.) | 163°–164° (dec.) | 175°–176° (dec.) | 140°–150° (dec.) |
| $[\alpha]_D^{23°}$ (c = 0.2 in methanol) | +111° | +107° | +139° | +122° |
| U.V. and Visible Spectra | | | | |
| $\lambda_{max}^{MeOH}$ | 228,260,418 nm | 228,260,418 nm | 228,260,418 nm | 228,260,418 nm |
| $E_{1\ cm}^{1\%}$ | 645,420,193 | 640,410,179 | 713,450,199 | 610,395,171 |
| $\lambda_{max}^{pH\ 7\ buffer}$ | 235,262,426 nm | 235,262,246 nm | 236,262,426 nm | 235,262,426 nm |
| $E_{1\ cm}^{1\%}$ | 600,406,161 | 605,400,160 | 617,424,166 | 580,400,160 |
| $\lambda_{max}^{0.01\ N\ NaOH}$ | 510 nm | 510 nm | 510 nm | 510 nm |
| $E_{1\ cm}^{1\%}$ | 120 | 118 | 128 | 110 |
| I.R. Spectrum (KBr): cm$^{-1}$ | 3,700–2,400 | 1,200 3,700–2,400 | 1,195 3,700–2,300 | 1,195 3,700–2,400 1,190 |
| | 1,725 | 1,180 1,665 | 1,180 1,710 | 1,180 |
| | 1,670 | 1,115 1,625 | 1,115 1,670 | 1,115 1,665 1,110 |
| | 1,625 | 1,085 1,585 | 1,625 | 1,040 |
| | 1,585 | 1,055 1,485 | 1,050 1,585 | 1,085 1,585 1,010 |
| | 1,490 | 1,015 1,470 | 1,010 1,490 | 1,010 1,485 980 |
| | 1,470 | 985 1,445 | 985 1,470 | 985 1,465 830 |
| | 1,450 | 940 1,420 | 940 1,445 | 835 1,445 750 |
| | 1,420 | 875 1,385 | 840 1,420 | 815 1,420 430 |
| | 1,385 | 840 1,325 | 820 1,385 | 795 1,385 |
| | 1,330 | 820 1,290 | 750 1,325 | 750 1,325 |
| | 1,300 | 795 1,235 | 435 1,295 | 435 1,295 |
| | 1,290 | 755 | 1,235 | 1,255 |
| | 1,240 | 440 | | 1,235 |
| Empirical Formula | $C_{27}H_{29}NO_{10}\cdot HCl$ | $C_{27}H_{31}NO_9\cdot HCl$ | $C_{27}H_{29}NO_9\cdot HCl$ | $C_{27}H_{31}NO_8\cdot HCl$ |
| Molecular Weight | 564 | 550 | 548 | 534 |

PURIFICATION PROCEDURE

Further purification of the antibiotic complex and its separation into its four components may be effected by silica gel column chromatography. The crude orange brown powder is dissolved in chloroform and the solution, mixed with an equivalent of methanolic hydrogen chloride, is chromatographed on silica gel with chloroform:methanol:water mixtures. The components D and C are eluted first, with a 94.8:5.0:0.2 mixture. The glycosides B and A follow with an 89.5:10.0:0.5 mixture. The components are usually separated as shown by paper and thin layer chromatography and the four components are obtained as their hydrochlorides in crystalline form.

CHEMICAL AND PHYSICAL PROPERTIES

The novel antibiotics of the invention have some common properties, but they can be distinguished on the basis of their chemical and physical characteristics. All the new anthracyclines have comparable solubility; as free bases they are soluble in chloroform, methylene dichloride, acetone, methanol, ethanol, aqueous alcohols, acidic water, dioxane and pyridine, but sparingly soluble or insoluble in diethyl ether, n-hexane, cyclohexane and petroleum ether. As hydrochlorides, they are soluble in water, methanol, ethanol and aqueous alcohols, but insoluble in acetone, benzene, chloroform, diethyl ether and petroleum ether. They can be used as indicators, being orange-yellow in neutral and acidic solutions, in which they also show orange-red fluorescence under U.V. light. Their alkaline solutions are red-brown, and when treated with alcoholic magnesium acetate they form red solutions. All these properties and the absorption spectra in the ultraviolet and visible regions, indicate that these new compounds are anthracycline antibiotics. The chemical and physical properties of glycosides A, B, C and D, isolated as the hydrochlorides are given in Table 3.

The new anthracycline antibiotics also show characteristic proton magnetic resonance (PMR) spectra. The spectrum of glycoside A, as the hydrochloride in DMSO-d$_6$, showed characteristic signals at 1.14δ (d, CH$_3$—C—5'), 3.39δ (s, CH$_3$O), 4.60δ (broad s, C-14-H$_2$) 4.89δ (broad s, C-7-H), 5.27δ (broad s, C—1'—H), 7.23δ (s, C—11—H), 7.4–7.9δ (m, C—1—H, C—2—N and C—3—H) and 13.61δ (s, C—6—OH) glycoside C, as the hydrochloride in DMSO-d$_6$, showed signals at 1.15δ (d, CH$_3$—C—5'), 2.26δ (s, CH$_3$CO), 3.92δ (s, CH$_3$O), 4.90δ (broad s, C—7—H), 5.26δ (broad s, C—1'—H) 7.31δ (s, C—11—H), 7.4–7.9δ (m, C—1—H, C—2H, and C-3-H) and 13.65δ (s, C—6—OH).

Field desorption mass spectroscopy of the free bases of glycosides A, B, C and D confirmed the assigned molecular formulae ,s shown in Table 4.

TABLE 4

| Compound | Molecular Formula | Molecular Weight Calculated | Found: m/c |
|---|---|---|---|
| GLYCOSIDE A | $C_{27}H_{29}NO_{10}$ | 527 | 527 (M$^+$) |
| GLYCOSIDE B | $C_{27}H_{31}NO_9$ | 513 | 514 (MH$^+$) |
| GLYCOSIDE C | $C_{27}H_{29}NO_9$ | 511 | 512 (MH$^+$) |
| GLYCOSIDE D | $C_{27}H_{31}NO_8$ | 497 | 498 (MH$^+$) |

Aqueous acid hydrolysis of glycosides A, B, C and D gives four different water insoluble yellow aglycones of the formulae V—VIII, above. The aqueous soluble fractions all contained the same reducing amino-sugar which was identified as daunosamine (3-amino-2,3,6-trideoxy-L-lyxohexose), the amino sugar component of daunomycin and adriamycin.

The structure of the aglycones were determined by analysis of their infrared, ultraviolet, visible, mass and magnetic resonance spectra. Their chemical and physical properties are reported in Table 5.

TABLE 5

Chemical and physical properties of the aglycones of glycosides A, B, C and D

| PROPERTY | AGLYCONE OF A | AGLYCONE OF B | AGLYCONE OF C | AGLYCONE OF D |
|---|---|---|---|---|
| Melting point °C. | 220 | 175–180 with decomposition | 213–215 | 175–180 with decomposition |
| $[\alpha]_D^{23°}$ (c = 0.1) | +161° (dioxan) | | +144° (methanol) | +164° (methanol) |
| U.V. e VIS Spectra $\gamma_{max}^{MeOH}$ | 227,259,418 nm | 227,258,413 nm | 227,258,418 nm | 227,258,418 nm |
| $E_{1\,cm}^{1\%}$ | 895,640,268 | 930,660,317 | 990,640,280 | |
| Empirical formula | $C_{21}H_{18}O_8$ | $C_{21}H_{20}O_7$ | $C_{21}H_{18}O_7$ | $C_{21}H_{20}O_6$ |
| Molecular weight calculated | 398 | 384 | 382 | 368 |
| Found m/e | 398 (M+) | 384 (M+) | 382 (M+) | 368 (M+) |

BIOLOGICAL ACTIVITY DATA

(a) Antibacterial acitvity

The "in vitro" minimum inhibitory concentrations (MIC) of glycosides A, B, C and D were determined for certain microorganisms using the standard tube dilution procedure and are reported in Table 6.

TABLE 6

| | MIC in μg/ml Glycosides | | | |
|---|---|---|---|---|
| Test Organism | A (I) | B (II) | C (III) | D (IV) |
| Staphylococcus aureus 209 P | 125 | 1000 | 62 | 250 |
| Staphylococcus aureus 153 | 500 | 1000 | 250 | 1000 |
| Sarcina lutea ATCC 9341 | 100 | 100 | 12.5 | 25 |
| Bacillus subtilis ATCC 6633 | 100 | 100 | 50 | 100 |
| Escherichia coli B | 50 | 100 | 25 | 50 |

(b) Antitumor activity

The new glycosides were tested against HeLa cells in vitro (time of exposure to the drugs: 24 hours) and on L 1210 and P 388 leukemia in mice in comparison with daunomycin. The results of the in vitro tests are given in Table 7. It can be seen therefrom that all the compounds inhibited the cell viability of HeLa cells in vitro, the ID$_{50}$ being 0.05 μg/ml for glycoside C, 0.1 μg/ml for glycoside A, 0.22 μg/ml for glycoside D and 0.44 μg/ml for glycoside B.

The in vivo data obtained in mice are reported in Table 8. Glycoside A was active against P 388 leukemia at a dose of 66 mg/kg, and toxic at a dose of 100 mg/kg. At the tolerated dose, the antitumor activity was greater than that of daunomycin.

TABLE 7

Effect on HeLa cells viability in vitro

| Compound | Dose(a) (ng/ml) | No. of colonies(b) % | ID$_{50}$ (ng/ml) |
|---|---|---|---|
| Daunomycin | 12.6 | 35–15 | 6–7 |
| | 6.25 | 48–66 | |
| | 3.12 | 71–80 | |
| Glycoside A (I) | 200 | 1 | |
| | 100 | 63 | 105 |
| | 50 | 73 | |
| | 25 | 74 | |
| Glycoside C (III) | 200 | 3 | |
| | 100 | 44 | 54 |
| | 50 | 54 | |
| Glycoside D (IV) | 400 | 0 | |
| | 200 | 53 | 220 |
| | 100 | 109 | |
| Glycoside B (II) | 1600 | 0 | |
| | 800 | 20 | 440 |
| | 400 | 66 | |

(a)HeLa cells were exposed to the drugs for 24 hours, then plated. Number of colonies was evaluated 5 days later.
(b)% over untreated controls.

TABLE 8

Effect against P 388 and L 1210 leukemia in mice

| Compound | Dose(a) (mg/kg) | T/C% L 1210 | T/C% P 388 | Toxic(b) deaths |
|---|---|---|---|---|
| Daunomycin | 2.9 | 133–133 | 190 | |
| | 4.4 | 140–133 | 200 | |
| | 6.6 | 111–133 | 223 | |
| Glycoside A (I) | 2.9 | 111 | | |
| | 6.6 | 128 | | |
| | 10 | 122 | | |
| | 66 | | 245 | |
| | 100 | | 254 | 1/10 |
| Glycoside C (III) | 2.9 | 100 | | |
| | 6.6 | 117 | | |
| | 15 | 122 | | |
| | 100 | | 181 | 3/8 |
| | 150 | | 45 | 3/19 |
| Glycoside D (IV) | 2.9 | 100 | | |
| | 6.6 | 100 | | |
| | 15 | 111 | | |
| | 125 | | 18 | 5/5 |
| | 250 | | 9 | 5/5 |
| Glycoside B (II) | 2.9 | 100 | | |
| | 6.6 | 122 | | |
| | 15 | 122 | | |
| | 500 | | 9 | 2/2 |

(a)Mice were treated intraperitoneally on day 1 after tumor cell inoculation.
(b)Evaluated on the basis of the macroscopic autopsy findings.

The following Examples are further illustrative of the invention.

EXAMPLE 1

The culture of *Micromonospora peucetica*, strain B 211 F.I., was grown for 25 days at 28° C. on agar slants of maintenance medium SA. Medium SA has the following composition: glucose 3%; brewers dry yeast 1.2%; sodium chloride 0.1%; potassium dihydrogen orthophosphate 0.05%; calcium carbonate 0.1%; magnesium sulphate 0.005%; ferrous sulphate heptahydrate 0.0005%; zinc sulphate heptahydrate 0.0005%; cupric sulphate pentahydrate 0.0005%; agar 2%; tap water up to 100%. Sterilization was carried out by heating in an autoclave at 120° C. for 20 minutes.

The mycelial mat of the culture so obtained was scraped off and suspended in 3 ml of sterile distilled water. The suspension was inoculated in 300 ml Erlenmeyer flasks containing 60 ml of the following liquid growth medium: brewers dry yeast 0.3%; peptone 0.5%; calcium nitrate tetrahydrate 0.05%; tap water up to 100%. Sterilization was effected by heating in an autoclave at 120° C. for 20 minutes. The pH of the medium after sterilization was between 6.8 and 7.0.

The inoculated flasks were shaken for 8 days at a temperature of 28° C. on a rotary shaker running at 250 rpm and describing a circle of 7 cm in diameter. 5 ml of the culture grown as described above were inoculated in a 300 ml Erlenmeyer flask containing 50 ml. of the following production medium: glucose 6%; brewers dry yeast 3%; sodium chloride 0.2%; potassium dihydrogen orthophosphate 0.1%; calcium carbonate 0.2% magnesium sulphate 0.01%; ferrous sulphate heptahydrate 0.001%; zinc sulphate heptahydrate 0.001%; cupric sulphate pentahydrate 0.001%; tap water up to 100%; sterilization by heating in autoclave at 115° C. for 20 minutes.

The flasks were incubated at 28° C. for 25 days under conditions identical to those described for the seed phase. The maximum concentration of the active compounds was reached between the 18th and 22nd days of fermentation with a production of 90 mcg/ml.

EXAMPLE 2

A culture of strain B 211 F.I. was grown for 14 days as described in Example 1, and the mycelial mat, collected as described in Example 1, was inoculated in 300 ml Erlenmeyer flasks containing 50 ml of the following liquid growth medium: soluble starch, 4%; soy bean flour 1.5%; brewer's dry yeast 0.5%, corn steep liquor 0.8%; calcium carbonate 0.3%; potassium monohydrogen orthophosphate 0.05%; magnesium sulphate 0.025%; potassium chloride 0.025%; tap water up to 100%. The pH, being 5.7 was brought to 7.5 with sodium hydroxide before sterilization. Sterilization was effected at 120° C. for 20 minutes.

After 4 days of incubation under the same conditions as described in Example 1, 5 ml of the thus grown culture were inoculated in 300 ml Erlenmeyer flasks containing 50 ml of the medium described above.

The flasks were then incubated under the same conditions as described above for 10 days. The maximum concentrations of the active compounds was reached between the 8th and 9th days of fermentation with a production of 15 mcg/ml.

EXAMPLE 3

The whole beer (20 liters) from a fermentation broth obtained according to Example 1, was adjusted to a pH of about 4 with hydrochloric acid and filtered, using 3% diatomaceous earth as a filter aid, to yield a cake and a filtrate which were extracted separately. The wet filter cake was treated with about 4 liters of a mixture of acetone and 0.1 N aqueous hydrochloric acid (80:20). After filtration, a second treatment with an additional 3 liters of acidified aqueous acetone assured complete extraction of the active compounds. The combined aqueous acetone extracts were adjusted with ammonium hydroxide to a pH of about 4, concentrated under reduced pressure to about 1 liter, and combined with the filtered broth. The obtained mixture was adjusted to a pH of about 8.5 to 9.0 and then extracted twice with one-half volume of a chloroform:methanol (9:1) mixture. The combined organic extracts were washed with water, dried on anhydrous sodium sulphate, and concentrated under reduced pressure to a volume of about 200 ml. By addition of 1 liter of n-hexane, the crude complex precipitated as a yellow brown powder (7 g).

EXAMPLE 4

A chloroform solution (6 g in 200 ml) of the crude complex (free base) after treatment with 10 ml of 1 N methanolic hydrogen chloride, was placed on a column of silicic acid (prepared in chloroform). The column was washed with chloroform, followed by elution with a chloroform:methanol:water mixture (94.8:5:0.2). The first yellow fraction contained some aglycones. The next two yellow bands contained, respectively, glycosides D and C. Elution was continued with a chloroform:methanol:water mixture (89.5:10:0.5) until two other yellow bands, corresponding to glycosides B and A, were eluted. The fractions containing these four bands were separately concentrated under reduced pressure to give substantially pure hydrochlorides of glycoside D (0.2 g), glycoside C (0.4 g), glycoside B (0.2 g) and glycoside A (0.6 g) as microcrystalline powders. Recrystallization of the glycosides A and C from methanol:butanol gave the corresponding pure hydrochlorides as yellow-orange crystals, m.p. 171°–173° C. with decomposition for glycoside A, m.p. 163°–164° C. with decomposition for glycoside B, m.p. 175°–176° C. with decomposition for glycoside C and m.p. 140°–150° C. with decomposition for glycoside D.

EXAMPLE 5

A 250 mg sample of glycoside A was dissolved in 10 ml of 0.2 N aqueous hydrochloric acid and the solution was heated for 1 hour at 95° C. A crystalline yellow-orange precipitate was collected by filtration after cooling, washed with water and dried over phosphorus pentoxide overnight under vacuum. 170 mg of the aglycone of glycoside A were obtained in pure form, m.p. 220° C., m/e: 398 (M+). After precipitation of the aglycone, the almost colorless aqueous acidic solution was adjusted to pH 5 with an anion exchange resin and then freeze-dried. The residue (60 mg), crystallized from methanol:acetone gave a crystalline compound, m.p. 166° C. with decomposition, identified as daunosamine hydrochloride by direct comparison with an authentic sample. Similar treatment of glycosides B, C and D yield the respective aglycones thereof.

Variations and modifications can, of course, be made without departing from the spirit and scope of the invention.

Having thus described our invention, what we desire to secure by Letters Patent and hereby claim is:

1. A process for producing an antibiotic complex including a mixture of the compounds having the formula:

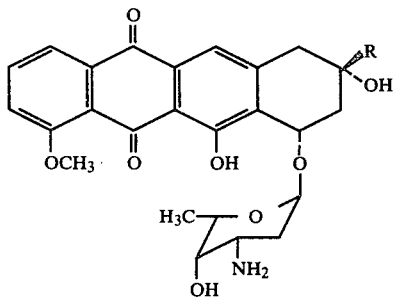

wherein R is —CO—CH₂OH, —CHOH—CH₃, —CO—CH₃ or —CH₂—CH₃ and a salt thereof, said process comprising cultivating the microorganism *Micromonospora peucetica* sp. nova under aerobic conditions in an aqueous culture medium containing an assimilable source of carbon, an assimilable source of nitrogen and mineral salts and recovering said antibiotic complex from the culture medium.

2. A process according to claim 1 wherein said cultivating is carried out for 5 to 30 days at a temperature of 25° to 37° C. and at a pH which is initially from 6.5 to 7.0 and which is from 6.5 to 8.0 at the end of the cultivating step.

3. A process according to claim 1 and further comprising removing the mycelium from the culture medium, separating the culture medium into solid and liquid phases and recovering said antibiotic complex from the mycelium, the solid phase and the liquid phase.

4. A process according to claim 1 and further comprising isolating from the antibiotic complex the individual glycosides 11-deoxy-adriamycin, 11-deoxy-13-dihydro-daunomycin, 11-deoxy-daunomycin, 11-deoxy-13-deoxo-daunomycin.

5. A process according to claim 4 wherein isolating is effected by silica gel column chromatography.

6. A biologically pure culture of the microorganism *Micromonospora peucetica* sp. *nova*, having the identifying characteristics of ATCC 31366, said culture being capable of producing anthracycline antibiotics in recoverable quantities.

* * * * *

UNITED STATES PATENT AND TRADEMARK OFFICE
CERTIFICATE OF CORRECTION

PATENT NO. : 4,309,503

DATED : January 5, 1982

INVENTOR(S) : Guiseppe Cassinelli, et al.

It is certified that error appears in the above—identified patent and that said Letters Patent is hereby corrected as shown below:

Column 4, line 12: "RSKOV", both instances, should read --ØRSKOV--.

Column 8, line 52: ",s" should read --as--.

Column 10, line 35: after "223", under heading "Toxic(b) deaths" insert --14/26--.

Signed and Sealed this

Fifteenth Day of February 1983

[SEAL]

Attest:

Attesting Officer

GERALD J. MOSSINGHOFF

Commissioner of Patents and Trademarks